United States Patent [19]

Kudo

[11] Patent Number: 5,075,529
[45] Date of Patent: Dec. 24, 1991

[54] ELECTROMAGNETIC SYRINGE NEEDLE DISPOSER

[75] Inventor: Yasushi Kudo, Tokyo, Japan

[73] Assignee: Takeshi Hirose, Shizuoka, Japan

[21] Appl. No.: 469,303

[22] Filed: Jan. 24, 1990

Related U.S. Application Data

[63] Continuation-in-part of Ser. No. 318,664, Mar. 3, 1989, abandoned.

[30] Foreign Application Priority Data

Oct. 17, 1988 [JP] Japan .................................. 63-135391

[51] Int. Cl.⁵ .............................................. H05B 6/10
[52] U.S. Cl. ................................ 219/10.77; 219/10.57; 219/7.5; 83/16; 83/944; 128/919
[58] Field of Search ....................... 219/10.57, 7.5, 9.5, 219/10.73, 10.75, 10.79, 10.77, 68; 128/303.1, 303.13, 303.14, 303.18, 303.19, 919; 29/403.4; 83/15, 16, 944; 604/199

[56] References Cited

U.S. PATENT DOCUMENTS

| | | | |
|---|---|---|---|
| 2,442,968 | 6/1948 | Bierwirth | 219/10.57 |
| 3,174,890 | 3/1965 | Goyke | 219/10.41 |
| 3,790,413 | 2/1974 | Kanetake | 219/10.57 |
| 3,796,849 | 3/1974 | Cuvelier | 219/10.41 |
| 4,115,681 | 9/1978 | Burley | 219/10.73 |
| 4,271,345 | 6/1981 | Palmer et al. | 219/10.79 |
| 4,492,840 | 1/1985 | Lex | 219/10.57 |
| 4,496,819 | 1/1985 | Acker et al. | 219/10.73 |
| 4,549,051 | 10/1985 | Ness | 219/10.57 |
| 4,628,169 | 12/1986 | Ching-Lung | 128/303.1 |
| 4,740,663 | 4/1988 | Roth et al. | 219/10.79 |

Primary Examiner—Philip H. Leung
Attorney, Agent, or Firm—Helfgott & Karas

[57] ABSTRACT

A syringe needle disposer includes a setting section for setting waste syringe needles and a magnetic field generating section for providing a high frequency alternating field to the setting section. When the high frequency alternating field is activated, a magnetic path of the magnetic flux passing through the waste syringe needle set in the setting section is formed, thereby induction-heating the syringe needle to soften the needle and to round its tip and to close an axial hole of the syringe needle. The sharp edge of the softened syringe needle may be blunted by contacting a pressure plate under pressure.

6 Claims, 5 Drawing Sheets

ELECTROMAGNETIC SYRINGE NEEDLE DISPOSER

CROSS REFERENCE TO A RELATED APPLICATION

This application is a continuation-in-part application of application Ser. No. 318,664 filed Mar. 3, 1989 now abandoned.

FIELD OF THE INVENTION

The present invention relates to a syringe needle disposer or destroyer, and more particularly to a syringe needle disposer for electromagnetic induction heating of waste syringe needles to sterilize them and to blunt their sharp edges.

BACKGROUND OF THE INVENTION

A conventional syringe needle disposer is disclosed, for example, in U.S. Pat. No. 4,628,169. The disposer is constructed as a mini electric syringe needle destroyer. This syringe needle destroyer is of electric resistance heating type, and in which a waste syringe needle is in contact with electrodes to apply a predetermined voltage to them, and to pass the electric current through the waste syringe needle for resistance heating the needle.

However, such a conventional syringe needle disposer has several disadvantages, i.e. (1) the electrodes are liable to be damaged because a large electric current is passed through the electrodes and occasionally, discharge takes place between the electrodes and the syringe needle; the waste needle is often cut in the part being in contact with the electrodes and thus, its axial hole for the passage of liquid still remains and the liquid remained in the syringe may be discharged after treating of the syringe needle.

SUMMARY OF THE INVENTION

Accordingly, it is an object of this invention to provide a syringe needle disposer having no electrodes damaged.

Another object of the invention is to provide a syringe needle disposer which can surely close an axial hole of the needle by induction heating to soften and to melt the needle.

The above objects can be achieved by a syringe needle disposer according to the present invention. The syringe needle disposer for heating waste syringe needles to sterilize them and to blunt their sharp edges comprises means for setting a syringe needle; means for generating a magnetic flux passing through said syringe needle, said magnetic flux being induced by an alternate electric current having a predetermined electric power and a predetermined frequency; and means for controlling the predetermined electric power and said predetermined frequency in accordance with a diameter of the syringe needles wherein said syringe needle is heated to have a round tip portion, thereby closing an axial hole of the needle in accordance with the magnetic flux passing therethrough.

The controlling means are constructed so as to control the generating means to generate the magnetic flux which is induced by the alternate electric current having a power of 2 to 4 KW and a frequency of 8 MHz, wherein said diameter is 0.5 to 2 mm.

Such a treatment of the waste syringe needle having a diameter ranging from 18 G to 25 G can be finished in about 1 to 1.5 seconds. A conventional resistance heating type of waste syringe needle requires about 0.5 second for finishing this treatment. By making such a time required for disposing the needle longer only by about 0.5 to 1 second, the axial hole of the molten and softened syringe needle is completely closed in the apparatus of the present invention. Because there is no part being in contact with an electrode, the disposer of the present invention can uniformly melt and soften the syringe needle over the full length of the needle without breaking the needle. In other words, due to melting and softening of the inner surface of the axial hole, it cannot keep its shape and thus is closed in at least one point in the direction of the needle. It is preferable to arrange the syringe needle horizontally for the purpose of only closing the hole of the needle. However, it is more desirable to arrange the syringe needle vertically by considering the facility in operation.

These and other objects, features and advantages of the present invention may be more clearly understood and appreciated from a review of the following detailed description of the disclosed embodiments and by reference to the appended drawings and claims.

The aforementioned objects, features and advantages of the invention will, in part, be pointed out with particularity, and will, in part, become obvious from the following more detailed description of the invention, taken in conjunction with the accompanying drawing, which form an integral part thereof.

DETAILED DESCRIPTION OF THE PREFERRED EMBODIMENTS

Figure 1:
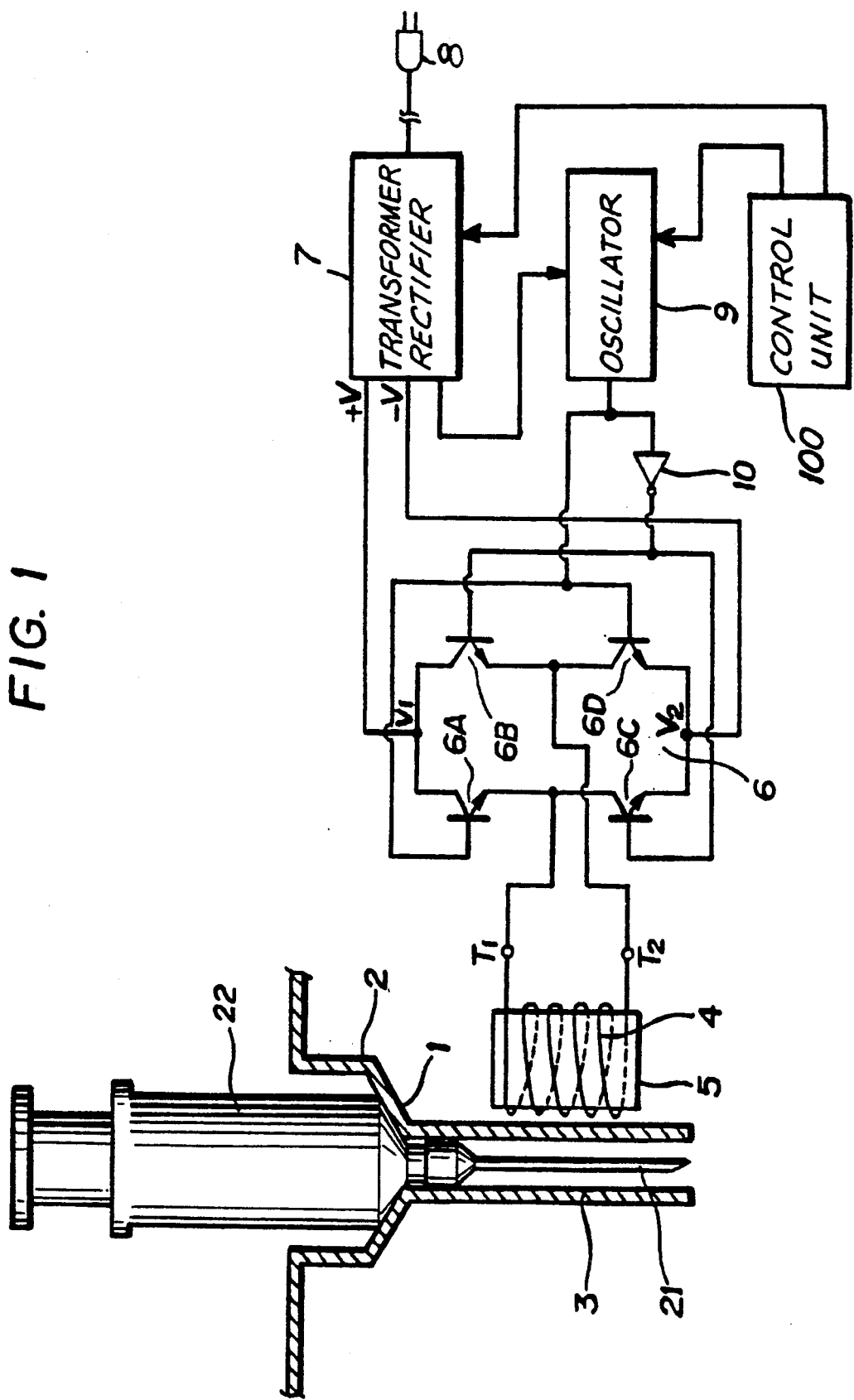
FIG. 1 is an explanatory view of a preferred embodiment in an electric circuit of the improved syringe needle dispenser of the present invention.

In FIG. 1, there is shown a waste syringe needle disposer according to the present invention and it comprises a syringe placing portion 2 having a conical bottom 1 and a syringe setting section 3 extending downwardly from the bottom 1. A coil 4 having a predetermined number of turns is provided adjacent to the syringe setting section 3. The coil 4 is wound around a magnetic core 5 and its terminals $T_1$ and $T_2$ are connected to a high voltage switching circuit 6. The high voltage switching circuit 6 comprises a bridge circuit consisting of four transistors 6A, 6B, 6C and 6D connected in series, and the voltage input points $V_1$ and $V_2$ of the circuit 6 are connected to positive and negative output terminals of a transformation/rectification circuit 7, respectively. The transformation/rectification circuit 7 is connected to a commercial power source of AC 100 V through a power source plug 8. The transformation/rectification circuit 7 transforms and rectifies from the AC voltage of 100 V to a DC voltage of 300 to 1000 V. The high voltage switching circuit 6 is connected at bases of four transistors 6A, 6B, 6C and 6D to an oscillator 9. The oscillator 9 is connected to a control unit 100 for controlling the same. Oscillator 9 generates a pulse ranging in frequency from 3 MHz to several MHz to be supplied directly to the transistors 6A and 6D, and through an inverter 10 to the transistors 6B and 6C.

Figure 2A:
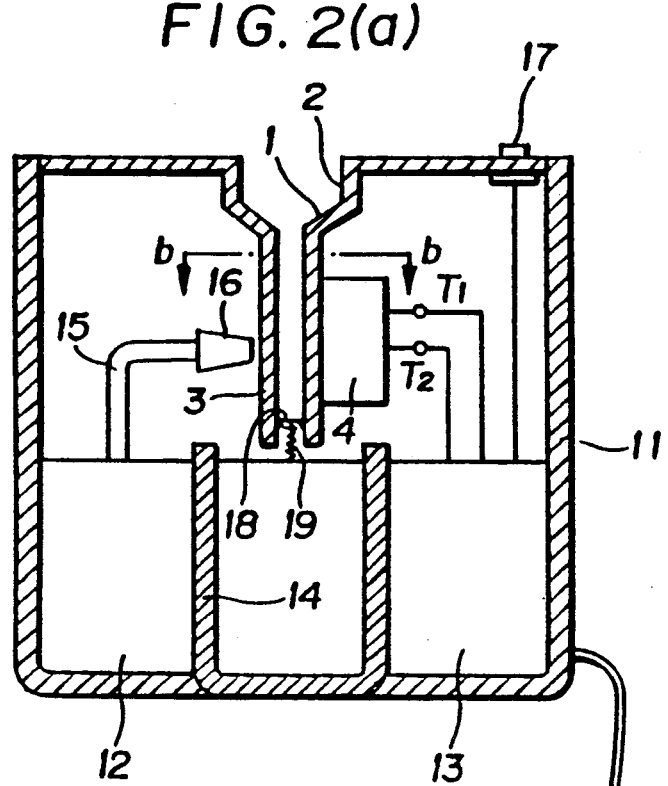
FIG. 2(a) is a sectional view of a preferred embodiment of the syringe needle disposer according to the present invention.

FIG. 2(a) shows a situation where the syringe needle disposer shown in FIG. 1 is received into a casing 11. In the bottom of the casing 11 are provided a cooling water channel 12 and a power source conduit 13, and a drawer 14 for drawing off the treated syringe needles is provided therebetween. The cooling water channel 12 is connected to a nozzle 16 through a hose 15, and the drawer 14 is designed in such a way that it can be drawn off in the direction perpendicular to the plane of the paper. The power source conduit 13 has the high voltage switching circuit 6, the transformation/rectification circuit 7, the oscillator 9 controlled by controlled unit 100 and the inverter 10 shown in FIG. 1, and it is activated with a switch 17.

Figure 2C:
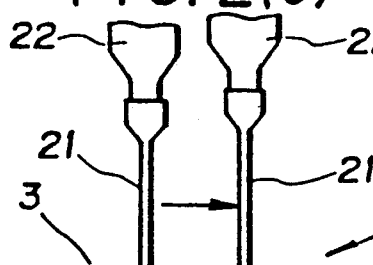
FIG. 2(c) is a sectional view of the syringe needle disposer taken along a line b—b shown in FIG. 2(a)
Figure 2B:
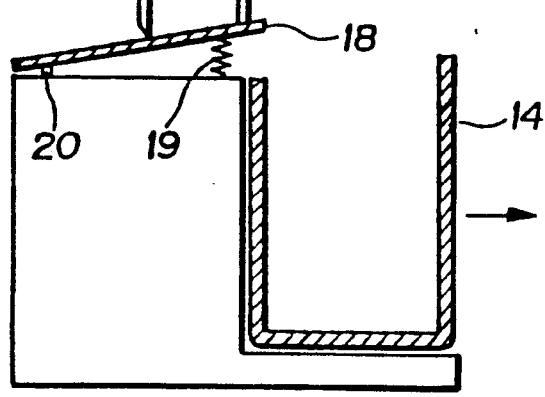
FIG. 2(b) is a sectional side elevation of the syringe needle disposer shown in FIG. 2(a)

FIG. 2(b) shows a sectional view taken along a line b—b in FIG. 2(a). The drawer 14 is positioned downwards a treated syringe needle discharge section 3A.

In FIG. 2(c) there is shown a pressure plate 18 provided in a syringe needle setting section 3, and the pressure plate 18 is activated upwardly by a spring 19 while being supported with a fulcrum 20.

In the operation of the waste syringe needle disposer according to the present invention, the power source circuit 13 is first activated by putting the switch 17 on. Then, the syringe 22 is displaced on the syringe placing portion 2 to set the waste syringe needle 21 in the syringe setting section 3 as shown in FIG. 1. This setting will permit the waste syringe needle 21 to be exposed to the high-frequency alternating field generated by the coil 4.

As a result, the syringe needle 21 is softened and partially melted by the induction heating and thus an axial hole of the needle 21 is closed.

Figure 3:
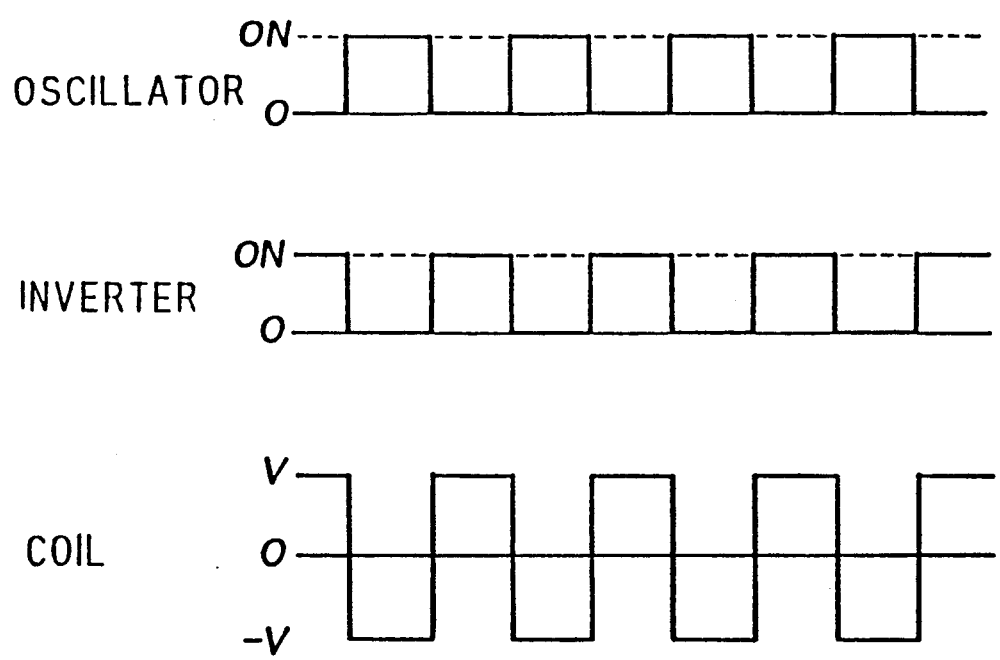
FIG. 3 is a timing chart showing the actuation of the syringe needle disposer of the present invention.
Figure 4A:
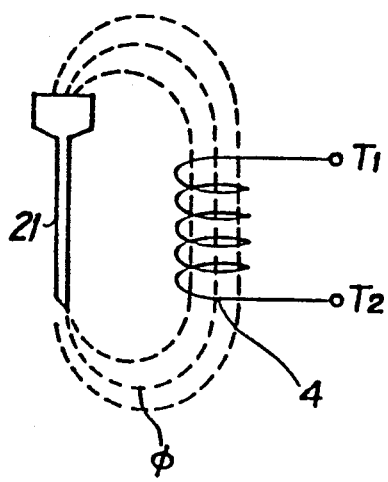
FIGS. 4(a)–4(d) are explanatory views showing the relationship between a coil and a syringe needle, respectively.
Figure 4B:
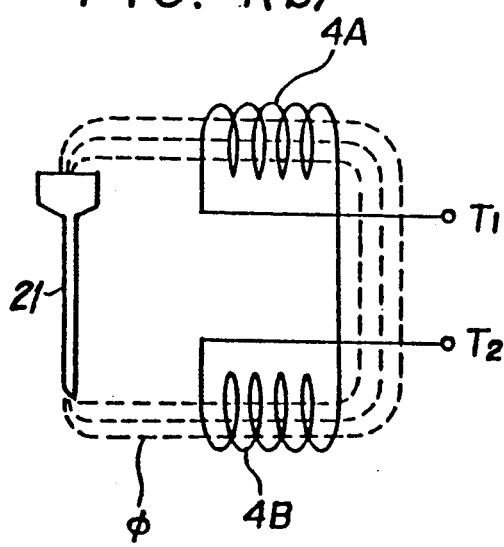
Figure 4C:
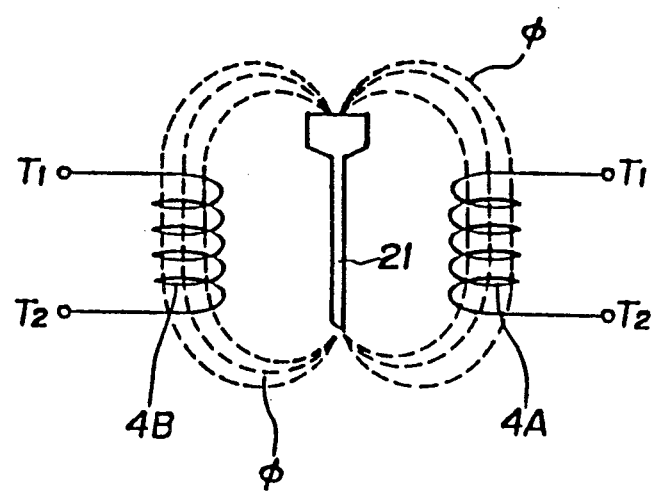
Figure 4D:
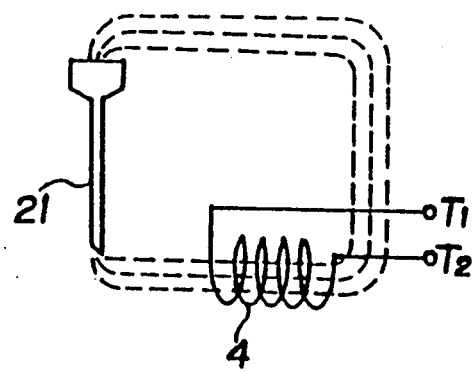

Then, the generation of the high-frequency alternating field shown in FIG. 3 will be described hereinafter. Upon ON-state of the switch 17, the transformation/rectification circuit 7 generates a direct current voltage of 2 V (−V to +V), and the oscillator 9 produces the high-frequency pulse shown in FIG. 3. This high-frequency pulse is applied to the transistors 6A and 6D in the high-voltage switching circuit 6, and the high-voltage pulse inverted by the inverter 10 is also applied to the transistors 6B and 6C. Consequently, the transistors 6A and 6D, and the transistors 6B and 6C are activated alternately, and the high-frequency alternating voltage shown in FIG. 3 is applied to the coil 4 from the transformation/rectification circuit 7, resulting in the generation of such a high-frequency alternating field from the coil 4.

The partially melted and softened syringe needle 21 is forced to be slid in the direction of the arrow as shown in FIGS. 2(b) and 2(c). This permits a sharp edge of the syringe needle to make contact with the surface of the pressure plate 18, thereby blunting the sharp edge of the needle and further closing the axial hole of the needle. When the syringe needle 21 is furthermore forced to be slid in the direction of the arrow, the syringe 22 can be dropped into the drawer 14 because the treated syringe needle discharge portion 3A adjacent to the syringe setting section 3 has an enlarged opening as shown in FIG. 2(b). Therefore, when the grasp of the syringe 22 by an operator is released, it may be dropped into the drawer 14. Because the drawer 14 can be pulled out in the direction of the arrow as shown in FIG. 2(c), the operator can treat and abandon the treated syringe needle without touching the needle 21.

FIGS. 4(a) to 4(d) show the magnetic relationship between a coil 4, 4A or 4B and a waste syringe needle 21, respectively. The magnetic lines of flux $\phi$ are passed through the needle 21 to form a magnetic path. The coil 4A wound in a given direction has the opposite direction to that of the coil 4B.

Figure 5A:
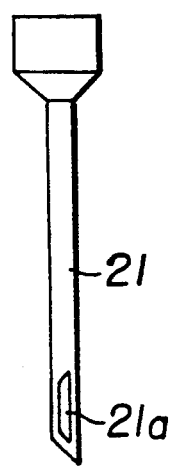
FIGS. 5(a)–5(c) show the syringe needle at three different stages for obtaining a round tip with a closed hole on the needle.
Figure 5B:
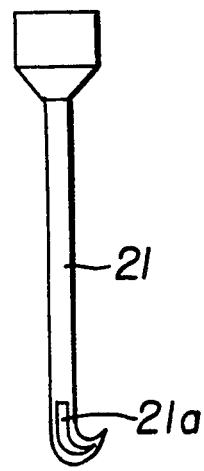
Figure 5C:
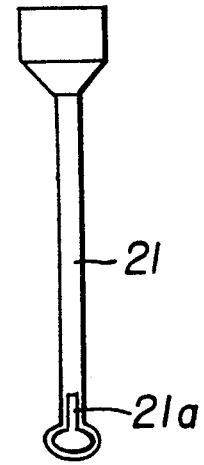

In the aforedescribed preferred embodiment, the pressure plate 18 may be omitted. Where the pressure plate 18 is not provided, frequency and power of the high frequency alternating field to which a syringe needle is exposed, are selected to range from 3 to 8 MHz and from 2 to 4 KW, respectively, thereby blunting a sharp edge of a syringe needle ranging in diameter from 0.5 to 2 mm and close an axial hole thereof. In more detail, where the frequency and the power of the high frequency alternating field are controlled in the above ranges, the syringe needle 21 is first heated to be red at the tip portion 21a as shown in FIG. 5(a), and the tip portion is then curved as shown in FIG. 5(b). Finally, the tip portion 21a of the syringe needle 21 becomes round to close the axial hole as shown in FIG. 5(c). Therefore, the provision of the syringe needle disposer with the pressure plate 18 becomes unnecessary due to selecting the frequency and the power. Where the frequency and the power is less than the lower limitation values, the syringe needle 21 is not melted, and where the frequency and the power exceeds the upper limitation values, the cost of a system and operation will be increased, in spite that effect remains in the same extent. This control is carried out by the aforementioned control unit 100 connected to the transformation and rectification circuit 7 and the oscillator 9.

As described above, the waste syringe needle disposer according to the present invention can surely close a needle axial hole for the passage of liquid without breaking the needle and having its composing parts damaged due to induction heating of the needle, based on a high-frequency alternating field.

The preferred embodiment of the present invention has been disclosed by way of example and it will be understood that other modifications may occur to those skilled in the art without departing from the scope and the spirit of the appended claims.

What is claimed is:

1. A syringe needle disposer, comprising:

means for receiving and supporting a syringe needle in a downwardly extended position within said means, said supporting means being formed so as to permit the needle, when forced, to slide in a horizontal direction;

means for generating a magnetic flux passing through said syringe needle placed in said supporting means so that said magnetic flux which is induced by an alternate electric current having a predetermined electric power and a predetermined frequency causes said syringe needle to at least partially melt by induction heating;

means connected to said generating means for controlling said generating means in accordance with a diameter of said syringe needle;

a pressure plate positioned in said supporting means and supporting thereon a tip of said syringe needle; and means for pressing said pressure plate against said needle so that, as said needle is partially melted and slid in said supporting means in the horizontal direction, an axial hole of said needle becomes completely closed.

2. A syringe needle disposer according to claim 1, wherein said supporting means includes a discharge portion for receiving said needle as the axial hole thereof has been completely closed; and further comprising a drawer positioned below said supporting means and receiving said needle from said discharge portion.

3. A syringe needle disposer according to claim 2, wherein said controlling means is electrically connected to said generating means to control said generating means to generate said magnetic flux which is induced by said alternate electric current having a power of 2 to 4 KW and a frequency of 3 to 8 MHz, wherein said diameter is 0.5 to 2 mm.

4. A syringe needle disposer according to claim 1, wherein said controlling means is electrically connected to said generating means to control said generating means to generate said magnetic flux which is induced by said alternate electric current having a power of 2 to 4 KW and a frequency of 3 to 8 MHz, wherein said diameter is 0.5 to 2 mm.

5. A syringe needle disposer according to claim 1, wherein said pressing means includes a spring biasing said pressure plate against the tip of the needle received in said supporting means.

6. A syringe needle disposer according to claim 5, wherein said pressure plate is supported in said supporting means in an inclined position.

* * * * *